US010154774B2

(12) United States Patent
Nishina et al.

(10) Patent No.: US 10,154,774 B2
(45) Date of Patent: Dec. 18, 2018

(54) ENDOSCOPE AND TREATMENT INSTRUMENT WITH LUBRICANT ELECTRODEPOSITION

(71) Applicant: OLYMPUS CORPORATION, Tokyo (JP)

(72) Inventors: Kenichi Nishina, Hachioji (JP); Toshihiko Hashiguchi, Sagamihara (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/286,802

(22) Filed: Oct. 6, 2016

(65) Prior Publication Data

US 2017/0020369 A1  Jan. 26, 2017

Related U.S. Application Data

(63) Continuation of application No. PCT/JP2015/061019, filed on Apr. 8, 2015.

(30) Foreign Application Priority Data

Apr. 16, 2014 (JP) ................................ 2014-084808

(51) Int. Cl.
*A61B 1/00* (2006.01)
*A61B 18/00* (2006.01)
*G02B 23/24* (2006.01)

(52) U.S. Cl.
CPC ............ *A61B 1/00075* (2013.01); *A61B 1/00* (2013.01); *A61B 1/0011* (2013.01);
(Continued)

(58) Field of Classification Search
CPC ... A61B 1/00075; A61B 1/00066; A61B 1/00; A61B 1/0011; G02B 23/24;
(Continued)

(56) References Cited

U.S. PATENT DOCUMENTS 4,532,924 A    8/1985  Auth et al.
4,855,077 A *  8/1989  Shikinami .............. C08G 18/12
                                                    252/500
(Continued)

FOREIGN PATENT DOCUMENTS

EP        1925335 A1      5/2008
JP        H05-307146 A   11/1993
(Continued)

OTHER PUBLICATIONS

International Search Report dated Jul. 7, 2015 issued in PCT/JP2015/061019.
(Continued)

*Primary Examiner* — John P Leubecker
*Assistant Examiner* — William Chou
(74) *Attorney, Agent, or Firm* — Scully, Scott, Murphy & Presser, P.C.

(57) ABSTRACT

An endoscope and a treatment instrument of the present invention include: an insertion portion that can be inserted into a subject; an electrodeposition portion provided on a surface of the insertion portion and configured to electrodeposit a lubricant applied to an outer surface; and a connection portion configured to connect the electrodeposition portion to one of a direct current power source and a static electricity generation apparatus in a state that the insertion portion is inserted into the subject.

4 Claims, 9 Drawing Sheets

(52) U.S. Cl.
CPC .......... *A61B 1/00066* (2013.01); *G02B 23/24* (2013.01); *G02B 23/2476* (2013.01); *G02B 23/243* (2013.01); *G02B 23/2446* (2013.01); *G02B 23/2484* (2013.01)

(58) Field of Classification Search
CPC . G02B 23/2476; A61L 29/14; A61L 2400/10; A61L 31/14; A61L 2202/24
USPC ....... 600/104, 109, 134, 138, 139, 153, 156, 600/160; 604/21, 264, 265
See application file for complete search history.

(56) References Cited

U.S. PATENT DOCUMENTS

| | | | |
|---|---|---|---|
| 5,928,159 | A | 7/1999 | Eggers et al. |
| 8,992,949 | B1 * | 3/2015 | Yang ...................... A61K 45/00 424/400 |
| 2007/0005024 | A1 | 1/2007 | Weber et al. |
| 2009/0216177 | A1 | 8/2009 | Akiyama et al. |
| 2009/0297581 | A1 | 12/2009 | Atanasoska et al. |
| 2010/0042205 | A1 * | 2/2010 | Atanasoska ............. A61L 31/10 623/1.38 |
| 2010/0191051 | A1 | 7/2010 | Miyake et al. |
| 2012/0253130 | A1 * | 10/2012 | Motoyama ........... A61B 1/0011 600/182 |
| 2015/0366610 | A1 * | 12/2015 | Tsuruta .............. A61B 1/00029 606/46 |
| 2016/0029998 | A1 * | 2/2016 | Brister ................ A61B 5/6853 600/424 |

FOREIGN PATENT DOCUMENTS

| | | |
|---|---|---|
| JP | H08-000543 A | 1/1996 |
| JP | H11-244375 A | 9/1999 |
| JP | 2000-254235 A | 9/2000 |
| JP | 2002-051967 A | 2/2002 |
| JP | 2004-057324 A | 2/2004 |
| JP | 2008-545511 A | 12/2008 |
| JP | 2011-177381 A | 9/2011 |
| WO | WO 2006/135755 A2 | 12/2006 |
| WO | WO 2007/032423 A1 | 3/2007 |
| WO | WO 2009/057191 A1 | 5/2009 |

OTHER PUBLICATIONS

Japanese Office Action dated May 24, 2016 issued in JP 2015-545591.
Extended Supplementary European Search Report dated Nov. 13, 2017 in European Patent Application No. 15 78 0738.9.

* cited by examiner

ENDOSCOPE AND TREATMENT INSTRUMENT WITH LUBRICANT ELECTRODEPOSITION

CROSS REFERENCE TO RELATED APPLICATION

This application is a continuation application of PCT/JP2015/061019 filed on Apr. 8, 2015 and claims benefit of Japanese Application No. 2014-084808 filed in Japan on Apr. 16, 2014, the entire contents of which are incorporated herein by this reference.

BACKGROUND OF INVENTION

1. Field of the Invention

The present invention relates to an endoscope and a treatment instrument including a rod-like insertion portion that can be inserted into a subject.

2. Description of the Related Art

When a medical tool, such as an endoscope and a treatment instrument, is inserted into a subject, such as a human body, a lubricant is applied to a surface of the medical tool in some cases as disclosed for example in Japanese Patent Application Laid-Open Publication No. 11-244375. By applying a lubricant on the surface of the medical tool, frictional resistance in moving the medical tool in the subject decreases, and discomfort of the subject can be reduced.

Some of the lubricants applied to the surface of the medical tool are gelatinous. Examples of known gel lubricants include lubricants containing Lidocaine or other anesthetics, such as Xylocaine Jelly, and lubricants not containing anesthetics, such as K-Y Jelly, Through Projelly, Endolubri (registered trademark), and CaineZero Jelly.

SUMMARY OF THE INVENTION

An aspect of the present invention provides an endoscope including: an insertion portion that can be inserted into a subject; a conductive electrodeposition portion exposed at at least part of a surface of the insertion portion and configured to electrodeposit a lubricant applied to an outer surface; a grasping portion for a user to grasp, the grasping portion being provided on a proximal end side of the insertion portion; an insulating member configured to electrically insulate the grasping portion from the electrodeposition portion; and a connection portion connected to a direct current power source configured to apply a voltage to the electrodeposition portion in a state that the insertion portion is inserted into the subject.

Another aspect of the present invention provides an endoscope including: an insertion portion that can be inserted into a subject; an electrodeposition portion configured to electrodeposit a lubricant applied to an outer surface, the outer surface including: a conductive portion provided on the insertion portion and made of a conductive material; and an insulating portion covering an outer surface of the conductive portion, exposed to a surface of the insertion portion, and made of an electrically insulating material; and a connection portion connected to a static electricity generation apparatus configured to cause the electrodeposition portion to take an electric charge in a state that the insertion portion is inserted into the subject.

An aspect of the present invention provides a treatment instrument including: an insertion portion that can be inserted into a subject; an electrodeposition portion configured to electrodeposit a lubricant applied to an outer surface, the outer surface including: a conductive portion provided on the insertion portion and made of a conductive material; and an insulating portion covering an outer surface of the conductive portion, exposed to a surface of the insertion portion, and made of an electrically insulating material; and a connection portion connected to a static electricity generation apparatus configured to cause the electrodeposition portion to take an electric charge in a state that the insertion portion is inserted into the subject.

DETAILED DESCRIPTION OF THE PREFERRED EMBODIMENT(S)

Figure 1:
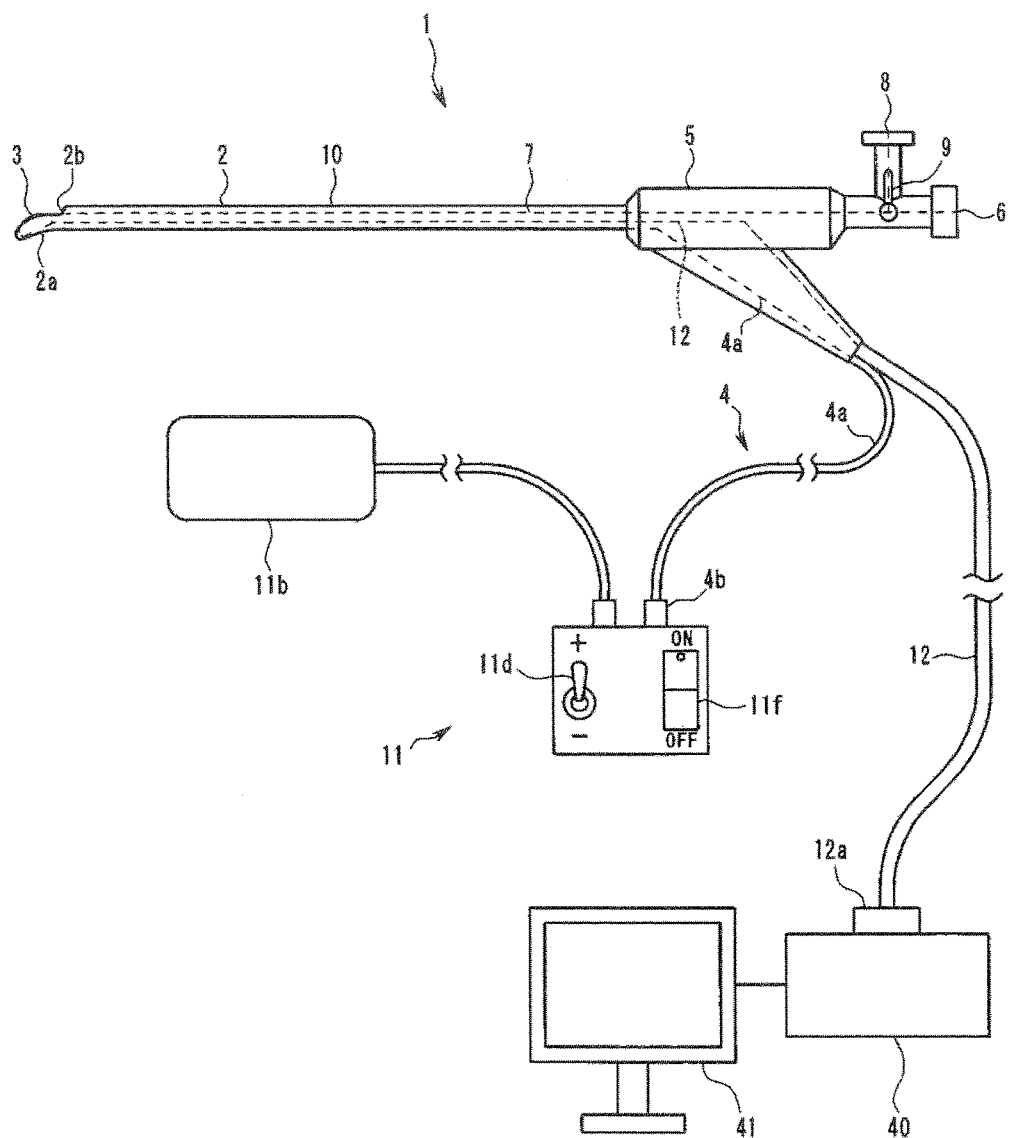
FIG. 1 is a diagram showing a configuration of an endoscope of a first embodiment.

Hereinafter, preferred modes of the present invention will be described with reference to the drawings. Note that scaling of each constituent element varies in each drawing used in the following description in order to illustrate each constituent element in a size that allows recognizing the constituent element on the drawing, and the present invention is not limited only to quantities of the constituent elements, shapes of the constituent elements, ratios of the sizes of the constituent elements, and relative positional relationships between respective constituent elements described in the drawings.

First Embodiment

As shown in FIG. 1, an endoscope 1 of the present embodiment includes an insertion portion 2, an observation portion 3, an electrodeposition portion 10, and a connection portion 4. For example, the endoscope 1 of the present embodiment includes a rod-like insertion portion 2 that can be inserted into a urethra of a human body that is a subject and includes, on a distal end portion 2a of the insertion portion 2, an observation portion 3 configured to observe inside of the subject.

Note that the endoscope 1 is not limited to a mode in which the insertion portion 2 is inserted into the urethra, and the endoscope 1 may be in a mode in which the insertion portion 2 is inserted into a trachea, a digestive tract, or other body cavities and tissues. Although the endoscope 1 is a so-called rigid endoscope in which the insertion portion 2 has a predetermined stiffness in an example of the present embodiment, the endoscope 1 may be a so-called flexible endoscope in which the insertion portion 2 has flexibility. When the insertion portion 2 has a predetermined stiffness, a shape of the insertion portion 2 is not limited to a linear shape, and the insertion portion 2 may have a bent shape. A cross section shape of the insertion portion 2 is not limited to a substantially circular or substantially square shape, and the shape may be a flat elliptical or rectangular shape.

A treatment instrument insertion channel 7 that is a tube-like member is located inside of the insertion portion 2 of the present embodiment, for example. One end of the treatment instrument insertion channel 7 is connected to an opening portion 2b provided on the distal end portion 2a of the insertion portion 2, and the other end of the treatment instrument insertion channel 7 is connected to a treatment instrument insertion port 6 and an irrigation water injection port 8 provided on a grasping portion 5 described later.

The grasping portion 5 is connected to a proximal end portion of the insertion portion 2. The grasping portion 5 is a part grasped by a user of the endoscope 1. The connection portion 4, the treatment instrument insertion port 6, and the irrigation water injection port 8 are provided on the grasping portion 5.

The connection portion 4 is a part configured to electrically connect the electrodeposition portion 10 described later to a power source section 11. Details of the connection portion 4 and the electrodeposition portion 10 will be described later.

The treatment instrument insertion port 6 and the irrigation water injection port 8 are opening portions connected to the treatment instrument insertion channel 7 that is a conduit located on the insertion portion 2. A cock 9 can be operated to switch a state in which the treatment instrument insertion channel 7 and the treatment instrument insertion port 6 are connected and a state in which the treatment instrument insertion channel 7 and the irrigation water injection port 8 are connected.

A treatment instrument, such as a puncture needle, can be inserted into the treatment instrument insertion channel 7 from the treatment instrument insertion port 6 to cause the treatment instrument to protrude from the opening portion 2b provided on the distal end portion 2a of the insertion portion 2. The irrigation water injection port 8 is a part configured to send a fluid into the subject through the treatment instrument insertion channel 7.

The observation portion 3 is a part configured to observe inside of the subject based on at least one of an optical image and an ultrasound image.

The observation portion 3 of the present embodiment includes, for example, a plurality of ultrasound transducers, and the part serves as an ultrasound transmission and reception portion configured to perform a scan with an ultrasound beam. The observation portion 3 is electrically connected to an observation apparatus 40 through an observation cable 12 passed through the insertion portion 2. More specifically, the observation cable 12 extends from the grasping portion 5 and is connected to the observation apparatus 40 through a connector portion 12a.

The observation apparatus 40 connected through the observation cable 12 controls operation of the observation portion 3. The observation apparatus 40 generates an ultrasound image from a signal obtained by driving the observation portion 3 and displays the ultrasound image on an image display apparatus 41.

Note that the form of the observation portion 3 included in the endoscope 1 is not limited to the present embodiment. For example, the observation portion 3 may be in a form of an electronic camera including an objective lens and an image pickup device. When the observation portion 3 is in a form of an electronic camera, the observation portion 3 is electrically connected to the observation apparatus 40 through the observation cable 12, and the observation apparatus 40 generates an optical image obtained by driving the observation portion 3 and displays the optical image on the image display apparatus 41. Note that when the observation portion 3 is configured to observe inside of the subject based on an optical image, an illumination section configured to emit illuminating light is located on the distal end portion 2a of the insertion portion 2.

The observation portion 3 may include, for example, both of the ultrasound transmission and reception portion and the electronic camera, and the observation apparatus 40 may be configured to display the ultrasound image and the optical image on the image display apparatus 41.

When the observation portion 3 is configured to observe inside of the subject based on the optical image, the observation portion 3 may include an objective lens and may be configured to transfer the optical image to an eyepiece located on the proximal end side of the insertion portion 2 through an optical fiber passed through the observation cable 12, for example.

The electrodeposition portion 10 is a part provided on the insertion portion 2 and configured to store an electric charge or take an electric charge to electrodeposit an electrically charged substance. In the present embodiment, the electrodeposition portion 10 is configured to store an electric charge to electrodeposit an electrically charged substance on a surface of the insertion portion 2, for example.

The electrodeposition portion 10 of the present embodiment is a member made of a conductive material exposed and provided around the insertion portion 2. The material forming the electrodeposition portion 10 is not particularly limited as long as the material is conductive, and for example, the material is a metal or a conductive resin.

Figure 2:
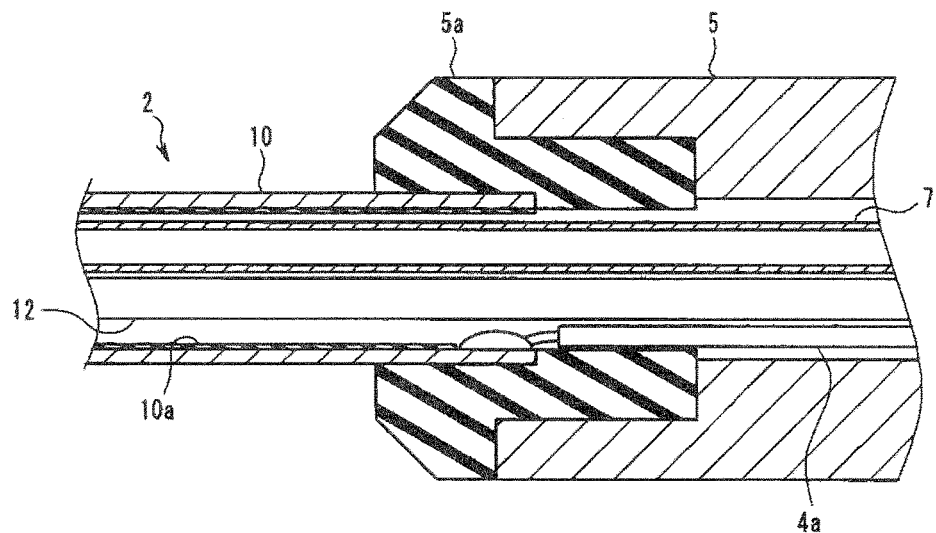
FIG. 2 is a cross-sectional view of an insertion portion and a grasping portion of the first embodiment.

As shown in a cross-sectional view of FIG. 2, the electrodeposition portion 10 is, for example, a metallic cylindrical member in the present embodiment. The electrodeposition portion 10 is exposed substantially across the entire outer surface of the insertion portion 2. More specifically, of the outer surface of the insertion portion 2, the electrodeposition portion 10 is provided in a region excluding regions in which the observation portion 3 and the opening portion 2b are located.

In the present embodiment, the electrodeposition portion 10 also functions as a structural member for the insertion portion 2 to have a predetermined stiffness, for example. A proximal end portion of the electrodeposition portion 10 is fixed to the grasping portion 5 through an insulating member 5a made of an electrically insulating material as shown in FIG. 2. Therefore, the electrodeposition portion 10 and the grasping portion 5 are electrically insulated.

Note that although the electrodeposition portion 10 is exposed across the entire outer surface of the insertion portion 2 in the present embodiment, the electrodeposition portion 10 may be exposed outward at a part of the outer surface of the insertion portion 2. That is, the outer surface of the insertion portion 2 may be formed by the electrodeposition portion 10 made of a conductive material and a member made of an electrically insulating material.

The electrodeposition portion 10 is electrically connected to the power source section 11 through the connection portion 4. More specifically, the connection portion 4 of the present embodiment includes a conductive cable 4a with a distal end portion connected to the electrodeposition portion 10. The distal end portion of the conductive cable 4a is connected to an inner circumferential surface of the cylindrical electrodeposition portion 10 through soldering or the like. The conductive cable 4a extends outside of the endoscope 1 from the grasping portion 5.

A connector portion 4b electrically connected to the power source section 11 described later is provided on a proximal end portion of the conductive cable 4a. The connector portion 4b may be directly connected to the power source section 11 or may be indirectly connected to the power source section 11 through another cable. The conductive cable 4a may be located only inside without extending outside of the endoscope 1, and the connector portion 4b may be provided on the outer surface of the grasping portion 5.

Note that although the conductive cable 4a extends from the grasping portion 5 at a same place as the observation cable 12 in the present embodiment as shown in FIG. 1, the conductive cable 4a and the observation cable 12 may extend from different places of the grasping portion 5.

An inner surface of the cylindrical electrodeposition portion 10 is covered by an insulating film 10a made of an electrically insulating material. The insulating film 10a electrically insulates the members located in the insertion portion 2, such as the observation cable 4a and the treatment instrument insertion channel 7, and the electrodeposition portion 10.

The power source section 11 is an apparatus configured to apply a voltage to the electrodeposition portion 10 or cause the electrodeposition portion 10 to take an electric charge. When the electrodeposition portion 10 is configured to store an electric charge, the power source section 11 is a direct current power source configured to apply a voltage to the electrodeposition portion 10. When the electrodeposition portion 10 is configured to take an electric charge, the power source section 11 is a static electricity generation apparatus configured to cause the electrodeposition portion 10 to take an electric charge.

Figure 3:
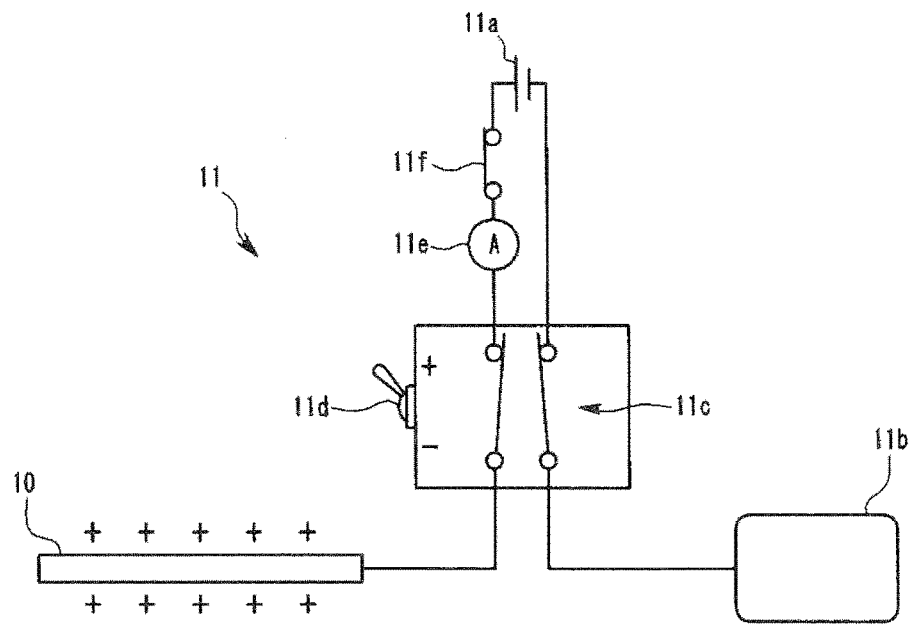
FIG. 3 is a diagram showing a configuration of a power source section of the first embodiment.

In the present embodiment, the electrodeposition portion 10 is configured to store an electric charge to electrodeposit an electrically charged substance on the surface of the insertion portion 2 as described above. Therefore, as shown in FIG. 3, the power source section 11 of the present embodiment includes a direct current power source section 11a configured to apply a voltage to the electrodeposition portion 10. The power source section 11 also includes a counter electrode plate 11b electrically connected to the direct current power source section 11a.

The counter electrode plate 11b is made of a conductive member and is electrically connected to the direct current power source section 11a through a conductive cable. The counter electrode plate 11b can be attached to a body surface of the subject. The direct current power source section 11a is electrically connected to the electrodeposition portion 10 through the conductive cable 4a. The direct current power source section 11a applies a voltage between the electrodeposition portion 10 and the counter electrode plate 11b.

The power source section 11 also includes: an operation switch 11f for the user to perform operation of starting and stopping the operation of the power source section 11; a polarity inversion portion 11c configured to switch a polarity of the voltage applied to the electrodeposition portion 10; a changeover switch 11d for the user to operate the polarity inversion portion 11c; and a restriction portion 11e configured to restrict an electric current outputted from the direct current power source section 11a.

Figure 4:
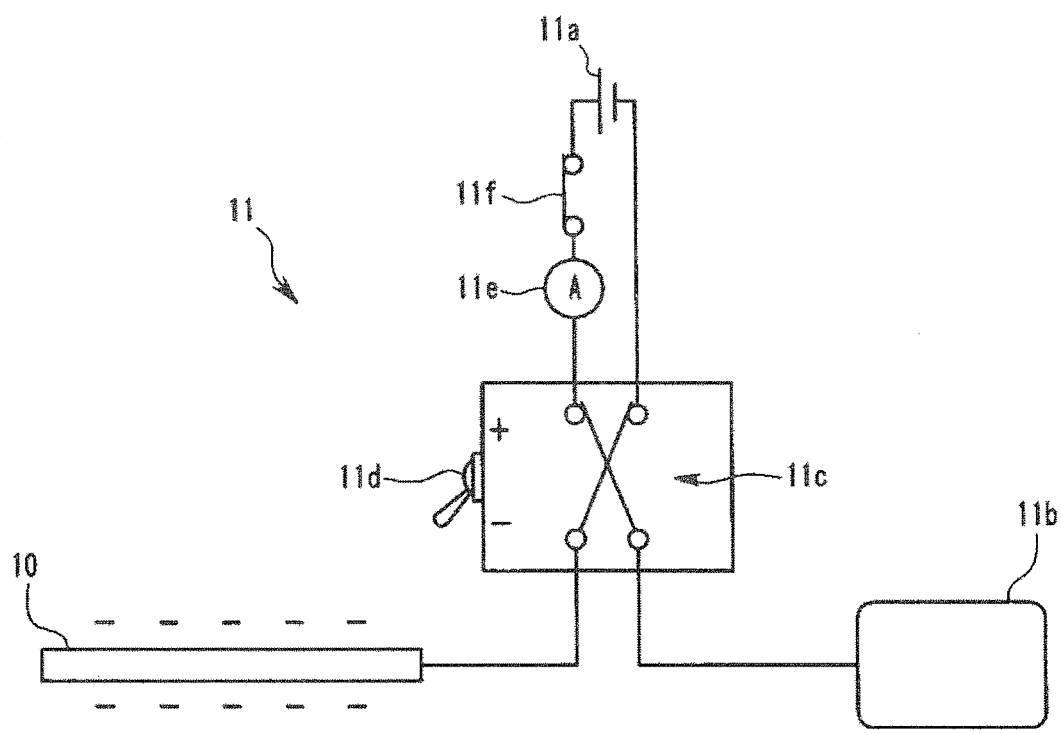
FIG. 4 is a diagram showing a configuration of the power source section of the first embodiment.

As shown in FIGS. 3 and 4, the polarity inversion portion 11c switches the polarity of the voltage applied to the electrodeposition portion 10 according to the operation of the changeover switch 11d by the user. In FIG. 3, the electrodeposition portion 10 is electrically connected to a positive pole of the direct current power source section 11a, and the counter electrode plate 11b is electrically connected to a negative pole of the direct current power source section 11a. The polarity inversion portion 11c is activated by operating the changeover switch 11d from the state of FIG. 3. As shown in FIG. 4, the electrodeposition portion 10 is electrically connected to the negative pole of the direct current power source section 11a, and the counter electrode plate 11b is electrically connected to the positive pole of the direct current power source section 11a.

In the state of FIG. 3, the electrodeposition portion 10 stores a positive electric charge based on the operation of the power source section 11. In the state of FIG. 4, the electrodeposition portion 10 stores a negative electric charge based on the operation of the power source section 11. In this way, the user can operate the changeover switch 11d to switch the polarity of the electric charge stored in the electrodeposition portion 10.

The restriction portion 11e detects an electric current value outputted from the direct current power source section 11a and cuts off the electric circuit when the electric current value exceeds a predetermined value. The restriction portion 11e is an apparatus configured to prevent an electric current with equal to or greater than a predetermined value from flowing in the subject that comes in contact with the insertion portion 2 and the counter electrode plate 11b.

Next, an action of the endoscope 1 with the configuration as described above will be described.

A gel lubricant is applied around the insertion portion 2 before the insertion portion 2 of the endoscope 1 is inserted into the urethra of the subject. Although the type of the lubricant is not particularly limited, examples of the gel lubricant for medical equipment include lubricants containing Lidocaine or other anesthetics, such as Xylocaine Jelly, and lubricants not containing anesthetics, such as K-Y Jelly, Through Projelly, Endolubri (registered trademark), and CaineZero Jelly.

The counter electrode plate 11b is attached to the body surface of the subject, such as belly, and the insertion portion 2 is inserted into the urethra. The operation switch 11f is turned on to start the operation of the power source section 11. As a result, the voltage is applied to the electrodeposition portion 10 provided on the insertion portion 2, and the electric charge is stored in the electrodeposition portion 10. Colloidal particles contained in the gel lubricant are generally electrically charged, and the colloidal particles contained in the lubricant applied to the surface of the insertion portion 2 are attracted by the electrodeposition portion 10.

In this way, the voltage is applied to the electrodeposition portion 10, and the lubricant containing the colloidal particles that are electrically charged substances is electrodeposited on the electrodeposition portion 10 in the present embodiment. Therefore, detachment of the lubricant from the surface of the insertion portion 2 can be prevented even when the insertion portion 2 is moved in the subject, such as in the urethra.

Note that the polarity of the electric charge of the colloidal particles varies depending on the material included in the lubricant. Therefore, the changeover switch 11d can be operated in the present embodiment to switch the polarity of the electric charge stored in the electrodeposition portion 10 to thereby electrodeposit the lubricant on the electrodeposition portion 10 regardless of the polarity of the charge of the colloidal particles.

In this way, an effect of the lubricant applied to the surface of the insertion portion 2 in the subject can be held for a longer time in the endoscope 1 of the present embodiment.

Second Embodiment

Hereinafter, a second embodiment of the present invention will be described. Only differences from the first embodiment will be described below. The same reference signs are provided to the same constituent elements as in the first embodiment, and the description will be appropriately omitted.

Figure 5:
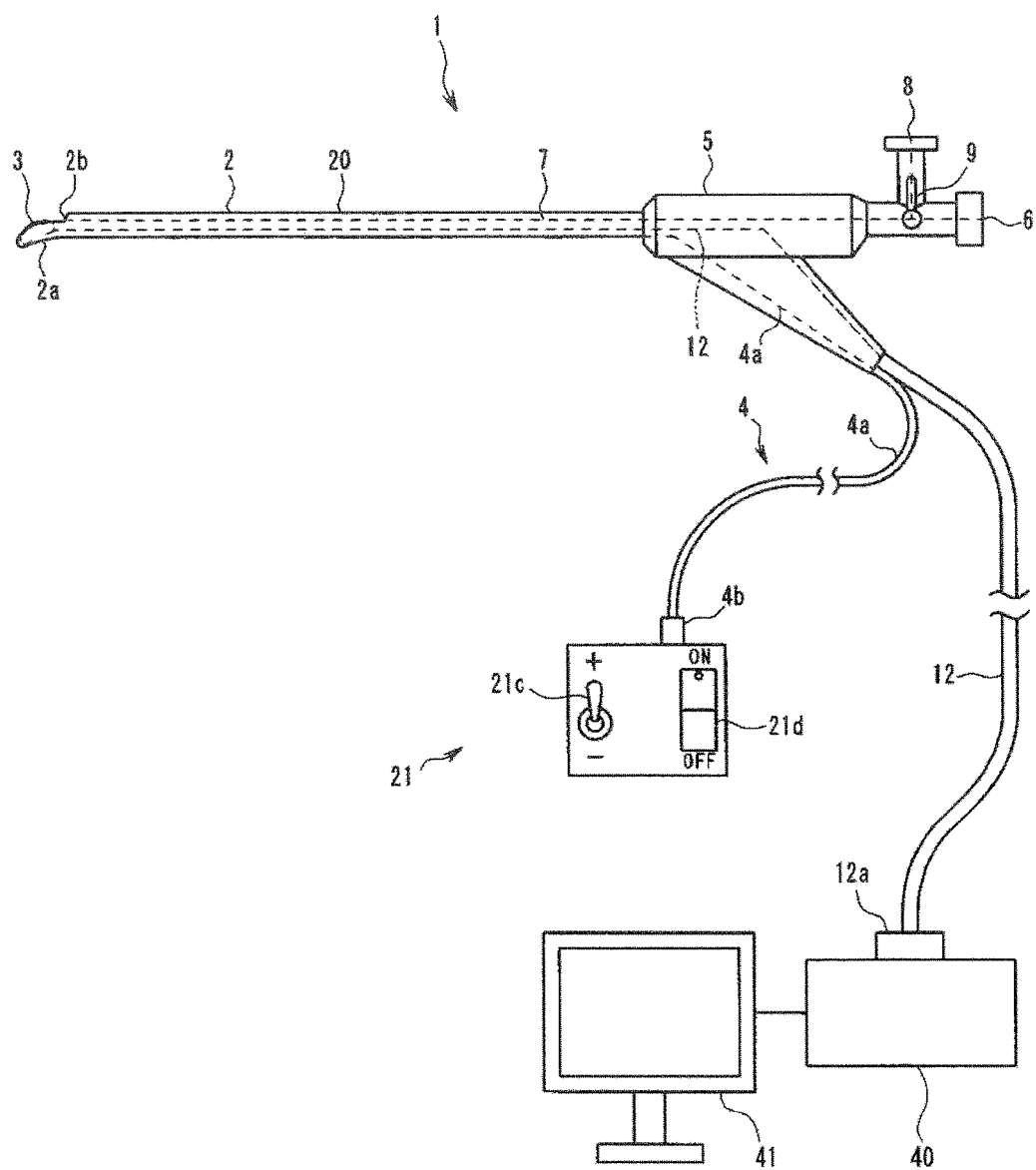
FIG. 5 is a diagram showing a configuration of the endoscope of a second embodiment.

In the present embodiment shown in FIG. 5, configurations of an electrodeposition portion 20 and a power source section 21 are different from the first embodiment. The electrodeposition portion 20 provided on the insertion portion 2 of the endoscope 1 of the present embodiment is configured to take an electric charge to electrodeposit an electrically charged substance on the surface of the insertion portion 2, for example.

Figure 6:
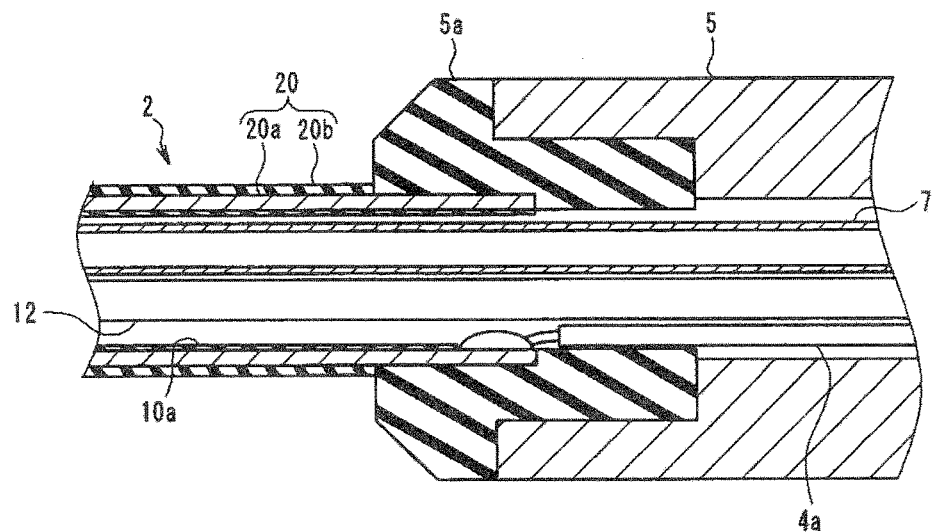
FIG. 6 is a cross-sectional view of the insertion portion and the grasping portion of the second embodiment.

As shown in a cross-sectional view of FIG. 6, the electrodeposition portion 20 is located on an outer circumferential portion of the insertion portion 2. The electrodeposition portion 20 of the present embodiment includes a conductive portion 20a and an insulating portion 20b.

The conductive portion 20a is a member made of a conductive material, such as a metal and a conductive resin, and located near the outer circumference of the insertion portion 2. In the present embodiment, the conductive portion 20a is, for example, a metallic cylindrical member.

In the present embodiment, the conductive portion 20a also functions as a structural member for the insertion portion 2 to have a predetermined stiffness, for example. A proximal end portion of the conductive portion 20a is fixed to the grasping portion 5 through the insulating member 5a made of an electrically insulating material. Therefore, the conductive portion 20a and the grasping portion 5 are electrically insulated.

The conductive portion 20a is electrically connected to the power source section 21 through the connection portion 4. More specifically, the connection portion 4 of the present embodiment includes the conductive cable 4a with the distal end portion connected to the conductive portion 20a. The distal end portion of the conductive cable 4a is connected to an inner circumferential surface of the cylindrical conductive portion 20a through soldering or the like. The conductive cable 4a extends outside of the endoscope 1 from the grasping portion 5.

The inner surface of the cylindrical conductive portion 20a is covered by the insulating film 10a made of an electrically insulating material. The insulating film 10a electrically insulates the members located in the insertion portion 2, such as the observation cable 4a and the treatment instrument insertion channel 7, and the conductive portion 20a.

The insulating portion 20b is a member made of an electrically insulating material, such as a resin, and exposed to the surface of the insertion portion 2. The insulating portion 20b covers an outer surface of the conductive portion 20a and electrically insulates the conductive portion 20a and the outside of the endoscope 1.

Figure 7:
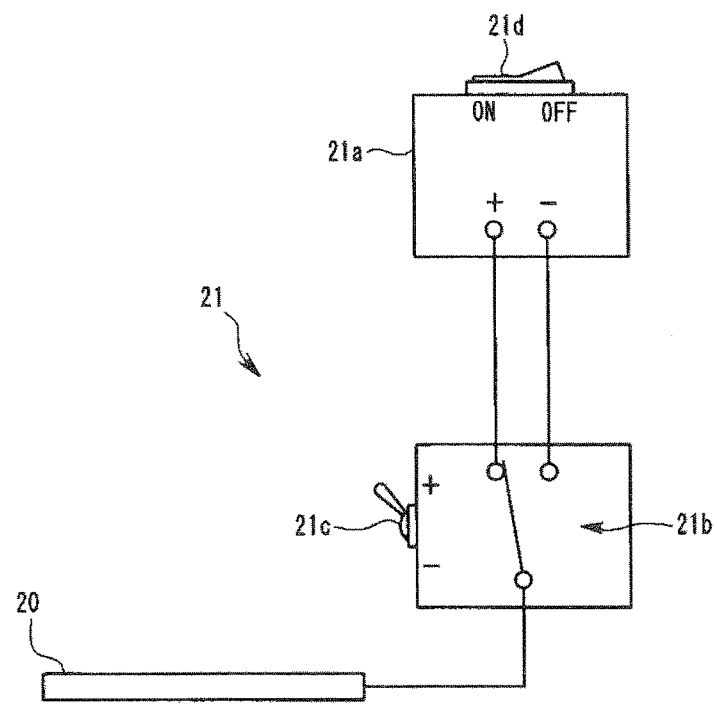
FIG. 7 is a diagram showing a configuration of a power source section of the second embodiment.

The power source section 21 of the present embodiment is an apparatus configured to cause the electrodeposition portion 20 to take an electric charge and includes a static electricity generation apparatus 21a as shown in FIG. 7. The power source section 21 also includes: an operation switch 21d for the user to perform operation of starting and stopping the operation of the power source section 21; a polarity inversion portion 21b configured to switch the polarity of the charge of the electrodeposition portion 20; and a changeover switch 21c for the user to cause the polarity inversion portion 21b to operate.

The electrodeposition portion 20 electrically connected to the power source section 21 takes an electric charge based on the operation of the power source section 21. The user can operate the changeover switch 21c to switch the polarity of the charge of the electrodeposition portion 20.

An action of the endoscope 1 of the present embodiment with the configuration as described above will be described.

A gel lubricant is applied around the insertion portion 2 before the insertion portion 2 of the endoscope 1 is inserted into the urethra of the subject. Although the type of the lubricant is not particularly limited, examples of the gel lubricant for medical equipment include lubricants containing Lidocaine or other anesthetics, such as Xylocaine Jelly, and lubricants not containing anesthetics, such as K-Y Jelly, Through Projelly, Endolubri (registered trademark), and CaineZero Jelly.

The operation switch 21d is operated to start the operation of the power source section 21. As a result, the electrodeposition portion 20 provided on the insertion portion 2 takes an electric charge, and colloidal particles contained in the lubricant applied to the surface of the insertion portion 2 are attracted by the electrodeposition portion 20.

In this way, the electrodeposition portion 20 is caused to take an electric charge, and the lubricant containing the colloidal particles that are electrically charged substances is electrodeposited on the electrodeposition portion 20 in the present embodiment. Therefore, detachment of the lubricant from the surface of the insertion portion 2 can be prevented even when the insertion portion 2 is moved in the subject, such as in the urethra.

Note that the polarity of the electric charge of the colloidal particles varies depending on the material included in the lubricant. Therefore, the changeover switch 21c can be operated in the present embodiment to switch the polarity of the electric charge of the electrodeposition portion 20 to thereby electrodeposit the lubricant on the electrodeposition portion 20 regardless of the polarity of the charge of the colloidal particles.

In this way, the effect of the lubricant applied to the surface of the insertion portion 2 in the subject can be held for a longer time in the endoscope 1 of the present embodiment.

Note that although the conductive portion 20a of the electrodeposition portion 20 is cylindrical and is arranged without a gap throughout the entire axial direction and circumferential direction of the insertion portion 2 in the present embodiment, the shape of the conductive portion 20a is not limited to the present embodiment.

Figure 8:
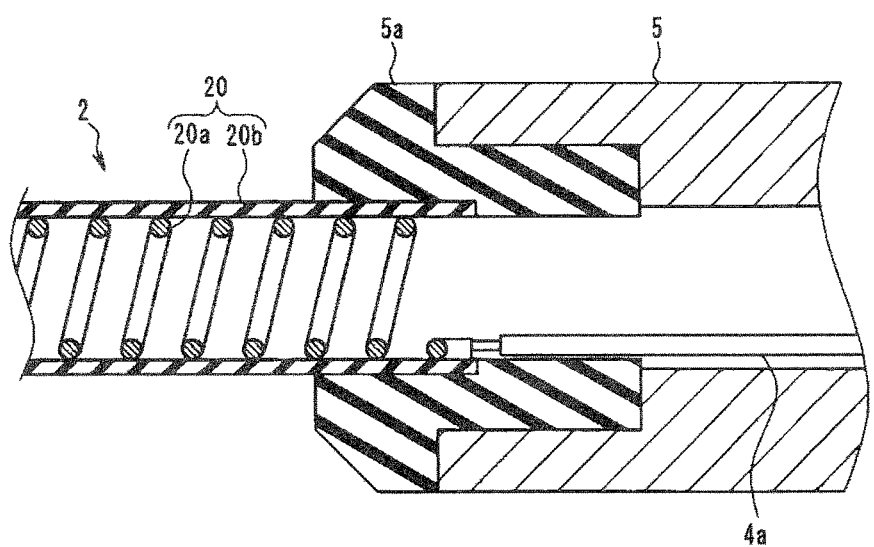
FIG. 8 is a cross-sectional view showing a modification of the endoscope of the second embodiment.

For example, as in a modification shown in FIG. 8, the conductive portion 20a may have a coil shape in which a linear member made of a conductive material is wound around a center axis of the insertion portion 2. In the modification of FIG. 8, the cylindrical insulating portion 20b is a structural member for the insertion portion 2 to have a predetermined stiffness, and the conductive portion 20a is wound around along an inner circumferential surface of the insulating portion 20b.

The electrodeposition portion 20 can also be caused to take an electric charge in the present modification, and the lubricant containing the colloidal particles can be electrodeposited on the electrodeposition portion 20 as in the embodiment described above. The conductive portion 20a can have a coil shape as in the present modification to make the electrodeposition portion 20 flexible. Therefore, the electrodeposition portion 20 can be easily applied to an endoscope with a flexible insertion portion.

Note that the electrodeposition portion 20 is not limited to the coil shape as shown in the figure, and the electrodeposition portion 20 may be formed by a linear member made of a conductive material arranged in a mesh.

Third Embodiment

Hereinafter, a third embodiment of the present invention will be described. Only differences from the second embodiment will be described below. The same reference signs are provided to the same constituent elements as in the second embodiment, and the description will be appropriately omitted.

Although the present invention is applied to the endoscope in the examples illustrated in the first and second embodiments, the present invention can be applied not only to the endoscope, but also to a treatment instrument that can be inserted into the subject. The present embodiment is an example in which the present invention is applied to a urethral catheter that is an example of the treatment instrument. Note that the treatment instrument according to the present invention is not limited to the urethral catheter, and the treatment instrument can be equipment noninvasively inserted from an anatomical opening of a human body, such as mouth, nose, ears, anus, vagina, and urethra. For example, the treatment instrument can be a tracheal suction catheter or the like inserted in-vivo from the mouth.

Figure 9:
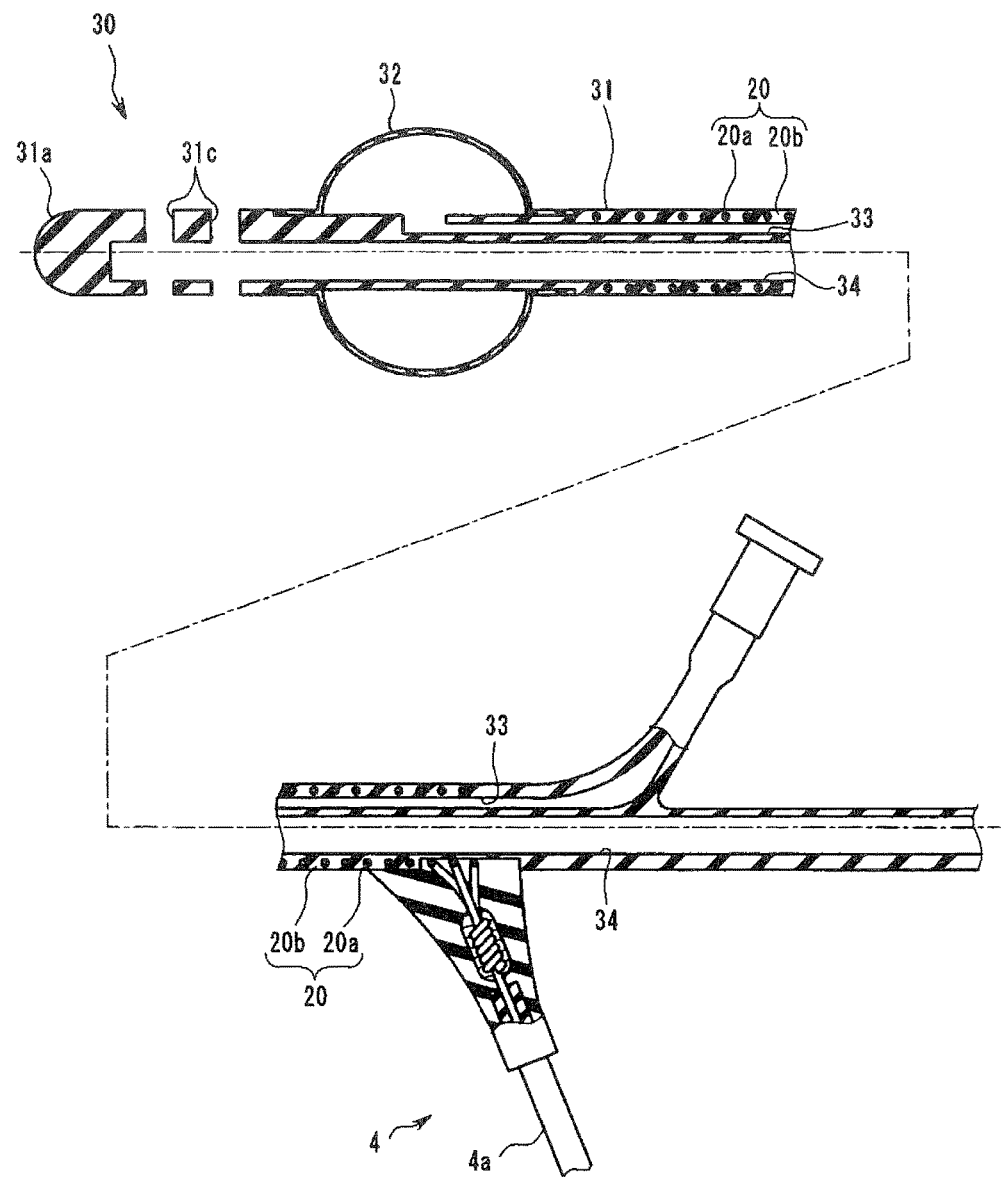
FIG. 9 is a cross-sectional view of a treatment instrument of a third embodiment.

A treatment instrument 30 of the present embodiment shown in FIG. 9 includes a rod-like insertion portion 31 that can be inserted into the urethra of a human body that is the subject.

A balloon conduit 33 and a urinary conduit 34 are formed in the insertion portion 31. The balloon conduit 3 is linked to inside of a balloon 32 provided on a distal end portion 31a of the insertion portion 31, and a fluid for inflating the balloon 32 in the subject can be sent into the balloon 32.

The urinary conduit 34 is a conduit connected to a urinary hole 31c provided on the distal end portion 31a of the insertion portion 31 and configured to discharge urine in the bladder. The other end of the urinary conduit 34 is connected to a bag or the like not shown that retains the urine.

The electrodeposition portion 20 is located on an outer circumferential portion of the insertion portion 31. The electrodeposition portion 20 includes the conductive portion 20a and the insulating portion 20b.

The conductive portion 20a is a member made of a conductive material, such as a metal and a conductive resin, and located near the outer circumference of the insertion portion 2. In the present embodiment, the conductive portion 20a is, for example, in a coil shape formed by winding a metallic wire. Note that the conductive portion 20a may be a conductive linear member arranged in a mesh. Forming the conductive portion 20a in a coil shape or a mesh shape can prevent the existence of the conductive portion 20a from obstructing curving of the insertion portion 31.

The conductive portion 20a is electrically connected to the power source section 21 not shown through the connection portion 4 provided on a proximal end side of the insertion portion 31. More specifically, the connection portion 4 of the present embodiment includes the conductive cable 4a with the distal end portion connected to the conductive portion 20a. The distal end portion of the conductive cable 4a is connected to the conductive portion 20a through soldering or the like.

The insulating portion 20b is a member made of an electrically insulating material, such as a resin, and exposed to the surface of the insertion portion 2. The insulating portion 20b covers the outer surface of the conductive portion 20a and electrically insulates the conductive portion 20a and the outside of the treatment instrument 30.

An action of the treatment instrument 30 of the present embodiment with the configuration as described above will be described.

A gel lubricant is applied around the insertion portion 31 before the insertion portion 31 of the treatment instrument 30 is inserted into the urethra of the subject. Although the type of the lubricant is not particularly limited, examples of the gel lubricant for medical equipment include lubricants containing Lidocaine or other anesthetics, such as Xylocaine Jelly, and lubricants not containing anesthetics, such as K-Y Jelly, Through Projelly, Endolubri (registered trademark), and CaineZero Jelly.

The operation switch 21d is operated to start the operation of the power source section 21. As a result, the electrodeposition portion 20 provided on the insertion portion 31 takes an electric charge, and colloidal particles contained in the lubricant applied to the surface of the insertion portion 31 are attracted by the electrodeposition portion 20.

In this way, the electrodeposition portion 20 is caused to take an electric charge, and the lubricant containing the colloidal particles that are electrically charged substances is electrodeposited on the electrodeposition portion 20 in the present embodiment. Therefore, detachment of the lubricant from the surface of the insertion portion 31 can be prevented even when the insertion portion 31 is moved in the subject, such as in the urethra.

In this way, in the treatment instrument 30 of the present embodiment, the effect of the lubricant applied to the surface of the insertion portion 31 in the subject can be held for a longer time as in the second embodiment.

Fourth Embodiment

Hereinafter, a fourth embodiment of the present invention will be described. Only differences from the first or second embodiment will be described below. The same reference signs are provided to the same constituent elements as in the first or second embodiment, and the description will be appropriately omitted.

The endoscope 1 of the present embodiment is different from the first or second embodiment in that a plurality of particle pockets 13 in a concave shape configured to hold electrically charged particulate substances are formed on the surface of the insertion portion 2.

Each of the plurality of particle pockets 13 includes an opening with a breadth that allows the colloidal particle contained in the gel lubricant for medical equipment to enter, and the particle pocket 13 has a depth with which part of the colloidal particle protrudes from the opening in a state that the colloidal particle has entered inside. That is, when the opening shape of the particle pocket 13 is approximated by a circle, the depth of the particle pocket 13 is a value smaller than a diameter of the circle approximating the opening shape. Here, the circle approximating the opening shape may be an inscribed circle of the opening shape or a circumscribed circle. The circle may have a diameter between diameters of the inscribed circle and the circumscribed circle.

The size and the depth of the opening of the particle pocket 13 are determined according to a diameter of the colloidal particles contained in the lubricant and are not limited. For example, the diameter of the colloidal particles is generally about 1 nm to 100 nm. Therefore, in an example of the present embodiment, the diameter of the particle pocket 13 is 150 nm or smaller, and the depth is 95 nm or smaller.

Figure 10:
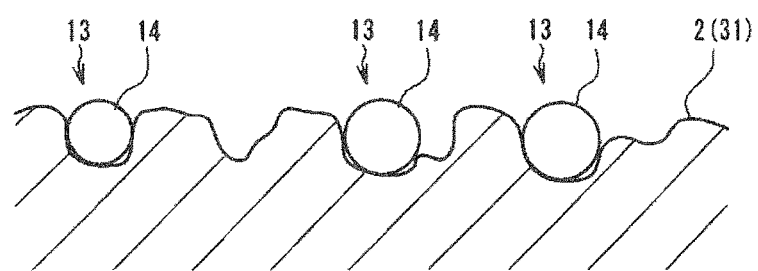
FIG. 10 is a cross-sectional view of particle pockets of fourth and sixth embodiments.

As shown in a cross-sectional view of FIG. 10, the particle pockets 13 of the present embodiment are formed such that the individual openings and depths are not constant, and the values are random. The plurality of particle pockets 13 in individually different shapes can be formed by chemical processing, such as etching, or mechanical processing, such as shot blasting. The shapes of the individual particle pockets 13 are different, and the particle pockets 13 can hold colloidal particles in various sizes. Note that the shapes of the plurality of particle pockets 13 may be substantially uniform.

In this way, the plurality of particle pockets 13 are formed on the surface of the insertion portion 2 of the endoscope 1 on which the electrodeposition portion 10 or 20 is located in the present embodiment. The plurality of particle pockets 13 have shapes that allow holding the colloidal particles contained in the gel lubricant for medical equipment. Therefore, when the lubricant is applied to the surface of the insertion portion 2, and colloidal particles of the lubricant are electrodeposited on the electrodeposition portion 10 or 20, the colloidal particles enter the particle pockets 13 and are held by the particle pockets 13.

Therefore, detachment of the lubricant from the surface of the insertion portion 2 is further prevented when the insertion portion 2 is moved in the subject. Part of the colloidal particles protrudes from the openings in the state that the colloidal particles of the lubricant are in the particle pockets 13. Therefore, the colloidal particles rotate between the tissue of the subject and the insertion portion 2 when the insertion portion 2 is moved in the subject, and frictional resistance between the tissue and the insertion portion 2 decreases.

Note that although the opening shapes of the particle pockets 13 can be approximated by circles in the description of the present embodiment, the shapes of the particle pockets 13 are not limited to these. For example, the particle pockets 13 may be grooves carved in a belt shape in the circumferential direction of the outer circumferential surface of the insertion portion 2. In this case, the particle pockets 13 have a groove shape in which the width is 150 nm or smaller, and the depth is 95 nm or smaller.

Fifth Embodiment

Hereinafter, a fifth embodiment of the present invention will be described. Only differences from the first, second, or fourth embodiment will be described below. The same reference signs are provided to the same constituent elements as in the first, second, or fourth embodiment, and the description will be appropriately omitted.

The endoscope 1 of the present embodiment is different from the first or second embodiment in that a plurality of concave portions 15 configured to hold the lubricant for medical tool are formed on the surface of the insertion portion 2.

Figure 11:
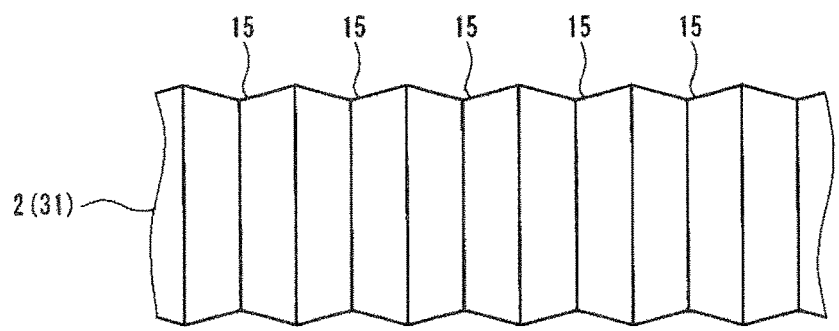
FIG. 11 is a diagram showing a shape of concave portions of fifth and seventh embodiments.

As shown in FIG. 11, in an example of the present embodiment, the plurality of concave portions 15 are V-shaped or U-shaped grooves carved in a belt shape in the circumferential direction on the outer circumferential surface of the insertion portion 2. The concave portions 15 that are belt-like grooves are arranged in the axial direction at predetermined intervals. Corner portions of places of valleys that are bottom portions of the concave portions 15 and places of mountains formed between adjacent concave portions 15 may be formed in a V-shape as shown in FIG. 11 or may have a shape rounded in a U-shape.

When the insertion portion 2 is inserted into the subject after applying the lubricant to the insertion portion 2 of the endoscope 1 of the present embodiment, the area that the tissue of the subject comes in contact with the surface of the insertion portion 2 becomes small because the concave portions 15 are formed on the surface of the insertion portion 2, and the frictional resistance between the tissue and the insertion portion 2 decreases. Furthermore, the lubricant is held in spaces in the concave portions 15, and the lubricant is supplied between the tissue of the subject and the surface of the insertion portion 2 from the inside of the concave portions 15 when the insertion portion 2 is moved in the subject. Therefore, the effect of the lubricant can be held for a longer time.

As described in the first and second embodiments, the electrodeposition portion 10 or 20 is provided on the insertion portion 2, and the colloidal particles of the lubricant are electrodeposited on the surface of the insertion portion 2. Therefore, detachment of the lubricant from the surface of the insertion portion 2 can be further prevented.

As described, the effect of the lubricant applied to the surface of the insertion portion 2 can be held for a longer time in the subject in the endoscope 1 of the present embodiment.

In addition to the concave portions 15, the plurality of particle pockets 13 configured to hold the colloidal particles of the lubricant described in the fourth embodiment may be formed on the surface of the insertion portion 2. The colloidal particles of the lubricant can be held in the particle pockets 13 by providing the particle pockets 13. Therefore, detachment of the lubricant from the surface of the insertion portion 2 can be further prevented, and the frictional resistance between the tissue and the insertion portion 2 can be reduced.

Figure 12:
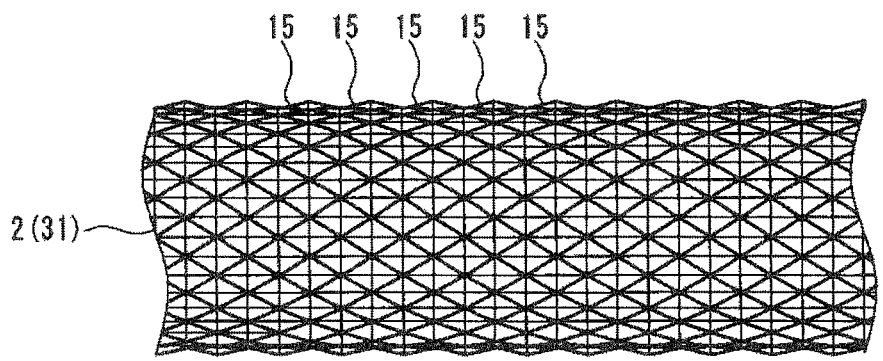
FIG. 12 is a diagram showing a first modification of the concave portions of the fifth and seventh embodiments.
Figure 13:
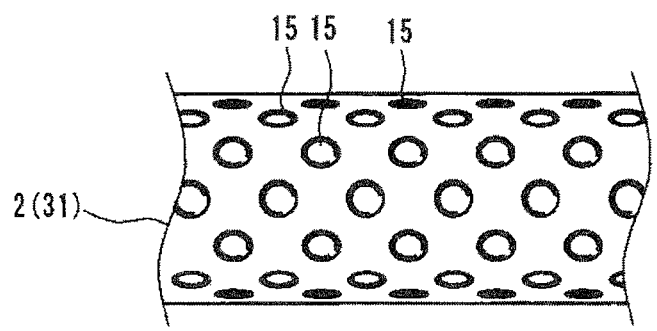
FIG. 13 is a diagram showing a second modification of the concave portions of the fifth and seventh embodiments.

Note that the shape of the concave portions 15 is not limited to the belt-like grooves carved in the circumferential direction of the insertion portion 2 as shown in FIG. 11. For example, the concave portions 15 may be a plurality of grooves carved in two intersecting directions as in a first modification shown in FIG. 12. The concave portions 15 may be, for example, hole-shaped in which outlines of the openings are closed as in a second modification shown in FIG. 13. When the concave portions 15 are hole-shaped, the arrangement of the concave portions 15 may be regular or may be random. The opening shape of the concave portions 15 is not particularly limited, and other than the illustrated circular shape, the shape may be polygonal or elliptical.

Sixth Embodiment

Hereinafter, a sixth embodiment of the present invention will be described. Only differences from the third embodiment will be described below. The same reference signs are provided to the same constituent elements as in the third embodiment, and the description will be appropriately omitted.

In the treatment instrument 30 of the present embodiment, the plurality of particle pockets 13 in the concave shapes configured to hold electrically charged particulate substances are formed on the surface of the insertion portion 31 of the treatment instrument 30 described in the third embodiment. The shapes of the particle pockets 13 are the same as the particle pockets 13 provided on the endoscope 1 in the fourth embodiment, and the same drawings as in the fourth embodiment will be used in the description.

Each of the plurality of particle pockets 13 includes an opening with a breadth that allows the colloidal particle contained in the gel lubricant for medical equipment to enter, and the particle pocket 13 has a depth with which part of the colloidal particle protrudes from the opening in the state that the colloidal particle has entered inside. That is, when the opening shape of the particle pocket 13 is approximated by a circle, the depth of the particle pocket 13 is a value smaller than the diameter of the circle approximating the opening shape. Here, the circle approximating the opening shape may be an inscribed circle of the opening shape or a circumscribed circle. The circle may have a diameter between the diameters of the inscribed circle and the circumscribed circle.

The size and the depth of the opening of the particle pocket 13 are determined according to the diameter of the colloidal particles contained in the lubricant and are not limited. For example, the diameter of the colloidal particles is generally about 1 nm to 100 nm. Therefore, in an example of the present embodiment, the diameter of the particle pocket 13 is 150 nm or smaller, and the depth is 95 nm or smaller.

As shown in the cross-sectional view of FIG. 10, the particle pockets 13 are formed such that the individual openings and depths are not constant, and the values are random. The plurality of particle pockets 13 in individually different shapes can be formed by chemical processing, such as etching, or mechanical processing, such as shot blasting. The shapes of the individual particle pockets 13 are different, and the particle pockets 13 can hold colloidal particles in various sizes. Note that the shapes of the plurality of particle pockets 13 may be substantially uniform.

In this way, the plurality of particle pockets 13 are formed on the surface of the insertion portion 31 of the treatment instrument 30 on which the electrodeposition portion 20 is located in the present embodiment. The plurality of particle pockets 13 have shapes that allow holding the colloidal particles contained in the gel lubricant for medical equipment. Therefore, when the lubricant is applied to the surface of the insertion portion 31, and colloidal particles of the lubricant are electrodeposited on the electrodeposition portion 10 or 20, the colloidal particles enter the particle pockets 13 and are held by the particle pockets 13.

Therefore, detachment of the lubricant from the surface of the insertion portion 31 is further prevented when the insertion portion 31 is moved in the subject. Part of the colloidal particles protrudes from the openings in the state that the colloidal particles of the lubricant are in the particle pockets 13. Therefore, the colloidal particles rotate between the tissue of the subject and the insertion portion 31 when the insertion portion 31 is moved in the subject, and frictional resistance between the tissue and the insertion portion 31 decreases.

Note that although the opening shapes of the particle pockets 13 can be approximated by circles in the description of the present embodiment, the shapes of the particle pockets 13 are not limited to these. For example, the particle pockets 13 may be grooves carved in a belt shape in the circumferential direction of the outer circumferential surface of the insertion portion 31. In this case, the particle pockets 13 have a groove shape in which the width is 150 nm or smaller, and the depth is 95 nm or smaller.

Seventh Embodiment

Hereinafter, a seventh embodiment of the present invention will be described. Only differences from the third or sixth embodiment will be described below. The same reference signs are provided to the same constituent elements as in the third or sixth embodiment, and the description will be appropriately omitted.

In the treatment instrument 30 of the present embodiment, the plurality of concave portions 15 configured to hold the lubricant for medical tool are formed on the surface of the insertion portion 31 of the treatment instrument 30 described in the third or sixth embodiment. The shape of the concave portions 15 is the same as the concave portions 15 provided on the endoscope 1 in the fifth embodiment, and the same drawings as in the fifth embodiment will be used in the description.

As shown in FIG. 11, the plurality of concave portions 15 are V-shaped or U-shaped grooves carved in a belt shape in the circumferential direction on the outer circumferential surface of the insertion portion 2. The concave portions 15 that are belt-like grooves are arranged in the axial direction at predetermined intervals. Corner portions of places of valleys that are bottom portions of the concave portions 15 and places of mountains formed between adjacent concave portions 15 may be formed in a V-shape as shown in FIG. 11 or may have a shape rounded in a U-shape.

When the insertion portion 31 is inserted into the subject after applying the lubricant to the insertion portion 31 of the treatment instrument 30 of the present embodiment, the area that the tissue of the subject comes in contact with the surface of the insertion portion 31 becomes small because the concave portions 15 are formed on the surface of the insertion portion 31, and the frictional resistance between the tissue and the insertion portion 31 decreases. Furthermore, the lubricant is held in spaces in the concave portions 15, and the lubricant is supplied between the tissue of the subject and the surface of the insertion portion 31 from the inside of the concave portions 15 when the insertion portion 31 is moved in the subject. Therefore, the effect of the lubricant can be held for a longer time.

As described in the third embodiment, the electrodeposition portion 20 is provided on the insertion portion 31, and the colloidal particles of the lubricant are electrodeposited on the surface of the insertion portion 31. Therefore, detachment of the lubricant from the surface of the insertion portion 31 can be further prevented.

As described, the effect of the lubricant applied to the surface of the insertion portion 31 can be held for a longer time in the subject in the treatment instrument 30 of the present embodiment.

In addition to the concave portions 15, the plurality of particle pockets 13 configured to hold the colloidal particles of the lubricant described in the sixth embodiment may be formed on the surface of the insertion portion 31. The colloidal particles of the lubricant can be held in the particle pockets 13 by providing the particle pockets 13. Therefore, detachment of the lubricant from the surface of the insertion portion 31 can be further prevented, and the frictional resistance between the tissue and the insertion portion 31 can be reduced.

Note that the shape of the concave portions 15 is not limited to the belt-like grooves carved in the circumferential direction of the insertion portion 2 as shown in FIG. 11. For example, the concave portions 15 may be a plurality of grooves carved in two intersecting directions as in a first modification shown in FIG. 12. The concave portions 15 may be, for example, hole-shaped in which outlines of the openings are closed as in a second modification shown in FIG. 13. When the concave portions 15 are hole-shaped, the arrangement of the concave portions 15 may be regular or may be random. The opening shape of the concave portions 15 is not particularly limited, and other than the illustrated circular shape, the shape may be polygonal or elliptical.

Note that the present invention is not limited to the embodiments, and the present invention can be appropriately changed within the scope or the spirit of the inventions that can be read from the claims and the entire specification. The changed endoscopes and treatment instruments are also included in the technical scope of the present invention.

What is claimed is:

1. An endoscope comprising:
    an insertion portion configured to be inserted into a subject;
    a conductive electrodeposition portion exposed at at least part of a surface of the insertion portion and configured to electrodeposit a lubricant applied to an outer surface;
    a grasping portion for a user to grasp, the grasping portion being provided on a proximal end side of the insertion portion;
    an insulating member configured to electrically insulate the grasping portion from the electrodeposition portion;
    a connection portion connected to the electrodeposition portion in a state that the insertion portion is inserted into the subject;
    a conductive counter electrode plate configured to be attached to a body surface of the subject in a state that the insertion portion is inserted into the subject; and
    a direct current power source connected to the connection portion and the counter electrode plate and configured to apply a voltage between the connection portion and the counter electrode plate.

2. The endoscope according to claim 1, wherein a plurality of particle pockets that are concave portions configured to hold electrically charged particulate substances are formed on the surface of the insertion portion.

3. The endoscope according to claim 2, wherein the particle pockets have opening shapes that allow particles with diameters equal to or smaller than 100 nm to enter, and depths of the particle pockets are equal to or smaller than 95 nm.

4. The endoscope according to claim 1, wherein an inner surface of the electrodeposition portion is covered by an electrically insulating film.

* * * * *